(12) United States Patent
Lammers

(10) Patent No.: US 7,487,800 B2
(45) Date of Patent: Feb. 10, 2009

(54) FLOW RESTRICTION

(75) Inventor: Leonardus Hubertus Maria Lammers, Hoofddorp (NL)

(73) Assignee: Solvist B.V., Hoofddorp (NL)

( * ) Notice: Subject to any disclaimer, the term of this patent is extended or adjusted under 35 U.S.C. 154(b) by 26 days.

(21) Appl. No.: 10/591,307

(22) PCT Filed: Feb. 10, 2005

(86) PCT No.: PCT/NL2005/000097

§ 371 (c)(1),
(2), (4) Date: Sep. 1, 2006

(87) PCT Pub. No.: WO2005/085700

PCT Pub. Date: Sep. 15, 2005

(65) Prior Publication Data

US 2007/0157986 A1    Jul. 12, 2007

(30) Foreign Application Priority Data

Mar. 3, 2004  (NL)  ................................. 1025624
Mar. 11, 2004 (NL)  ................................. 1025697

(51) Int. Cl.
*F24H 9/12* (2006.01)
(52) U.S. Cl. .............................. 138/37; 138/39; 604/407
(58) Field of Classification Search .................. 138/37, 138/39, 44; 604/407, 403
See application file for complete search history.

(56) References Cited

U.S. PATENT DOCUMENTS

| | | | |
|---|---|---|---|
| 2,409,294 A * | 10/1946 | Martin | 138/44 |
| 2,484,418 A * | 10/1949 | Mercier | 138/44 |
| 4,136,692 A | 1/1979 | Goldowsky | 604/251 |
| 4,256,132 A * | 3/1981 | Gunter | 137/14 |
| 4,654,026 A * | 3/1987 | Underwood | 604/80 |
| 5,315,859 A * | 5/1994 | Schommer | 73/1.25 |
| 5,341,848 A | 8/1994 | Laws | 138/44 |
| 5,409,477 A * | 4/1995 | Caron et al. | 604/407 |
| 5,449,350 A * | 9/1995 | Lasaitis et al. | 604/246 |
| 5,499,968 A | 3/1996 | Milijasevic et al. | 604/30 |
| 6,740,077 B1 | 5/2004 | Brandau et al. | 604/892.1 |

FOREIGN PATENT DOCUMENTS

| | | |
|---|---|---|
| DE | 19704497 | 11/1997 |
| EP | 1150738 | 7/2001 |
| WO | WO 96/23534 | 8/1996 |
| WO | WO 97/24528 | 7/1997 |

* cited by examiner

*Primary Examiner*—Patrick F Brinson
(74) *Attorney, Agent, or Firm*—Abelman, Frayne & Schwab

(57) ABSTRACT

Flow restriction to be fitted in a fluid line, consisting of a conduit part that has been produced from plastic by injection moulding and has been provided with a baffle closing the flow cross-section, wherein one or more openings have been made with the aid of a laser treatment. Each of these openings has a diameter of between 1 and 50 μm. It has been found that, when a large number of openings are used, if one of the openings becomes blocked for whatever reason this has hardly any effect on the total flow cross-sectional surface area. It is consequently possible to determine the flow conditions in the restriction very accurately and very reproducibly and consequently to establish the flow characteristics accurately. Such a flow restriction can be used, for example, in applications for dosing medication.

15 Claims, 2 Drawing Sheets

FLOW RESTRICTION

The present invention relates to a flow restriction according to the precharacterizing clause of claim 1. Such a flow restriction is disclosed in DE 197 04 497. In this specification an infusion pump for a drug that is implanted in a patient is described. With this arrangement there is a perfusion plate that serves as flow impedance. This is made, for example, of plastic by making openings therein using a laser beam. The plate is incorporated in the tubing in a manner that is not described in more detail.

A flow meter for liquids, where a thin plate is used, which plate is clamped/welded into the lumen, is disclosed in U.S. Pat. No. 4,136,692.

The aim of the present invention is to provide a flow restriction that can easily be employed, can be incorporated in a reliable and advantageous manner in a fluid line, functions reliably and can be produced inexpensively. The inexpensive production and the reliable construction give rise, inter alia, to the possibility of using such a reliable flow restriction in products that are intended for one-off use.

This aim is realized with a flow restriction as described above having the characterizing features of claim 1.

According to the present invention conduit part and baffle are made from one piece of plastic material. Preferably these are produced in one operation by injection moulding. As a result a flow restriction that is very small can be made in a highly reproducible manner, whilst a particularly reliable join to the tubing is formed.

Moreover, the problem of handling small discs with openings is solved by means of the invention. After all, these discs can be particularly small and thin, which makes handling difficult, even apart from hygiene requirements that are imposed in the case of medical applications.

According to a particular variant of the invention, this is made such that there is a predictable relationship between the pressure applied to the tubing and the flow caused as a result.

Preferably, this relationship is linear and more particularly it satisfies Poiseuille's equation. This is valid for laminar liquid flow in a cylindrical conduit of radius r. If there is a pressure difference $\Delta p$ over the length 1, the volume flow rate is:

$$q_v = \Pi r^4 \Delta p / 8 \eta 1$$

As a result it is possible, for example, to determine the flow rate at a specific viscosity and density of the liquid by reading off the pressure, for example the height of the liquid column. This is important in particular when administering a wide variety of medicinal substances to patients. As a result of making the flow restriction according to the invention in one piece, there are no longer construction limitations with respect to the baffle. After all, in the state of the art this baffle had to have sufficient strength for clamping or sufficient material thickness to enable subsequent welding. However, on the other hand, it is important that this baffle can be drilled through easily, such as with the aid of laser beams. By means of the present invention the design of the baffle can mainly be focused on enabling it to be drilled through in an optimum manner during a subsequent laser treatment.

According to the present invention the flow restriction consists of a conduit part. A baffle is arranged in this. Subsequently, according to the present invention, one or more openings with a diameter dimension of between 1 and 50 µm, more particularly 5 and 40 µm, are made in said baffle. Diameter dimension is to be understood below as a cross-sectional surface area resolved to a circular opening with a diameter of between 1 and 50 µm. However, it will be understood that the opening(s) can have any desired shape. As a result of making a number of openings, in the event of blockage of one of the openings the effect of the blockage of one of the openings will be relatively restricted, depending on the number of openings. By making openings of very small diameter it is possible to meter even very small amounts of fluid (both gas and liquid). Furthermore, use of the restriction is appreciably facilitated because this is in one piece with a conduit part that can be employed in the customary manner.

According to a first variant embodiment, this conduit part can be coupled to further conduit parts, which can be fitted either inside it or around it. However, it is possible to make the conduit part a part of any other member, such as a coupling. Especially in medical technology, such items as Luer fittings are used for joining conduit parts to one another. By arranging a restriction in such a fitting, as is proposed according to the invention, it is not necessary to work with additional components. It will be understood that the restriction according to the present invention can also be made in any other conceivable manner.

The wall thickness of the baffle is between 0.05 and 0.5 mm and more particularly is between 0.1 and 0.3 mm. With laser techniques it is possible to make openings in such a film. During this operation the plastic material vaporizes/disintegrates, so that making openings does not result in residues that could block the openings being left. As a result of the use of the laser techniques described above for making openings, the risk of blockages by impurities is precluded and in principle it is also not necessary to check for these.

The baffle can be made of any plastic material known in the state of the art and in particular consists of a polycarbonate film.

According to an advantageous embodiment of the invention there are at least 10 openings in the baffle and more particularly more than 100 openings. Such openings can easily be produced by the use of a mask that is placed in the path between the laser and the baffle. In this way a large number of openings can be produced in one or a few steps.

Furthermore, it is possible to make these openings such that they are not cylindrical, but divergent, in the longitudinal direction thereof. That is to say the cross-sectional dimension of the openings becomes increasingly larger in the direction of flow. Blockage of the openings is counteracted by this means.

Using the present invention it is possible to meter very small amounts of liquid. 0.5 ml/h is mentioned as an example. The result of this is that, for example, 100 ml of an analgesic can be administered directly into a wound over a period of 7 days, with a simple pump, in a reliable manner. Moreover, the passage of a large amount of solvent (such as water) into the patient is prevented, so that it is possible to work with concentrated solutions.

In addition to the characteristics of color and length, the invention offers many more and clearer identification means for a specific type of restriction, such as, for example, a different shape for conduit parts that do not have a sealing function in the liquid line, or printing, or laser engraving. The latter two can display either a value or a symbol. With such identification the user is able to see what is the "yield" of a specific restriction. Clearly differentiating identification means prevent errors in the assembly of administration systems and thus errors in the administration of medication to patients.

Moreover, with the restriction described above it is possible, within certain limits, to measure the flow through the conduit part. By determining the pressure difference over the accurate and relatively substantial restriction, a low flow can be determined very accurately. The consequence of the accurate restriction is also that it is now also possible to use pressure-controlled equipment instead of volumetric pumps for accurate administration of, for example, infusion liquids. It has been found that variations are essentially linear within the specific limits described above.

It is also possible to position a number of the restrictions described above, which may or may not have a different "value", one after the other. By this means it is possible to obtain an even greater resistance to flow, without this being at the cost of reliability. After all, as indicated above, blockage of one of the many openings will have no effect.

The laser used for making the openings can be a laser that works in the ultraviolet range, such as an excimer laser. However, it must be understood that other types of lasers can be used.

The invention will be explained in more detail below with reference to some illustrative embodiments shown in the drawings. In the drawings:

FIG. 1 shows, diagrammatically in cross-section, a first embodiment of the restriction;

FIGS. 2a-d show various embodiments of the openings;

Figure 1:
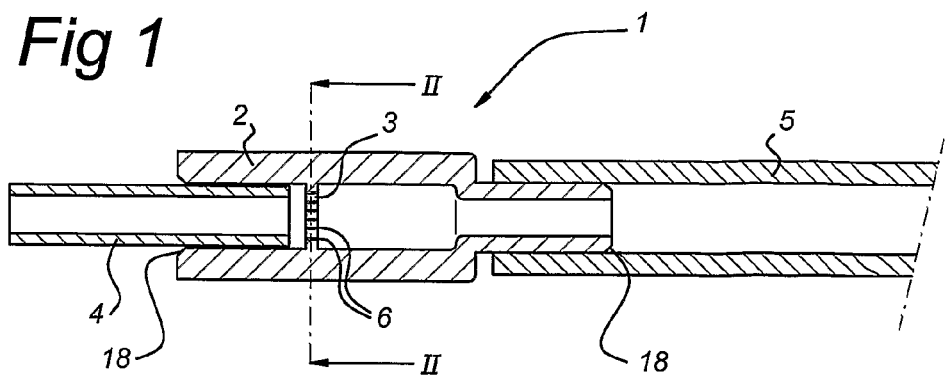

In FIG. 1 the restriction according to the invention is indicated in its entirety by 1. This consists of a conduit part 2 and a baffle 3 arranged therein. Conduit part 2 and transverse baffle 3 are made of one material, in particular polycarbonate material, and more particularly are made in one part by injection moulding. An inlet conduit 4 is pushed into the conduit part 2 on the left, whilst on the right an outlet conduit 5 has been pushed over it. Conduit part 2 is provided with self-seeking edges 18, as a result of which the introduction of inlet conduit 4 and pushing on outlet conduit 5, respectively, is facilitated. These edges are important because as a result flexible conduits that are somewhat oversize and undersize, respectively, can be used that provide sealing between the flexible conduit and the conduit part.

There are a large number of openings 6 in the transverse baffle 3. This can be seen from FIGS. 2a-d. For the sake of simplicity the openings have been drawn relatively large, but it must be understood that these have a small size of between 1 and 50 µm and more particularly approximately 5-40 µm. In practice hundreds to thousands of openings will be used. The accuracy of such openings is particularly high in the case of production with laser techniques. With the relatively small diameter of the opening, the length thereof is substantial. In this context the length is preferably in any event at least so chosen that laminar flow prevails in the openings. More particularly, a length/diameter ratio of greater than 10 is chosen in order to make such a flow laminar.

Figure 2A:
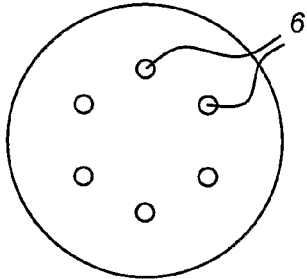
Figure 2B:
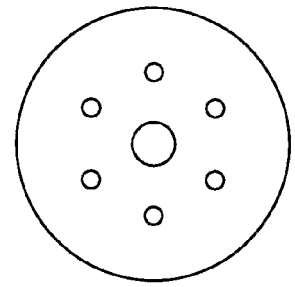
Figure 2C:
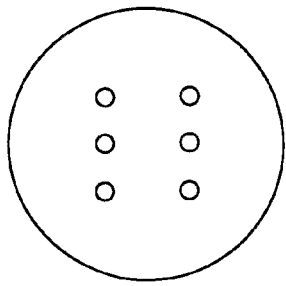
Figure 2D:
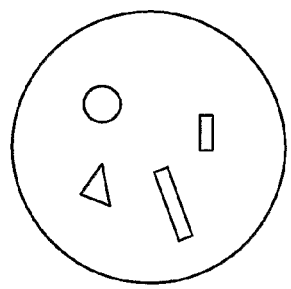

Circular openings all with the same diameter have been drawn in FIG. 2a. In FIG. 2b circular openings of different diameter have been drawn. Both in FIG. 2a and 2b the openings are grouped around the midpoint of the restriction. In FIG. 2c a different pattern is shown, whilst in FIG. 2d openings made in a different way are shown.

Figure 3:
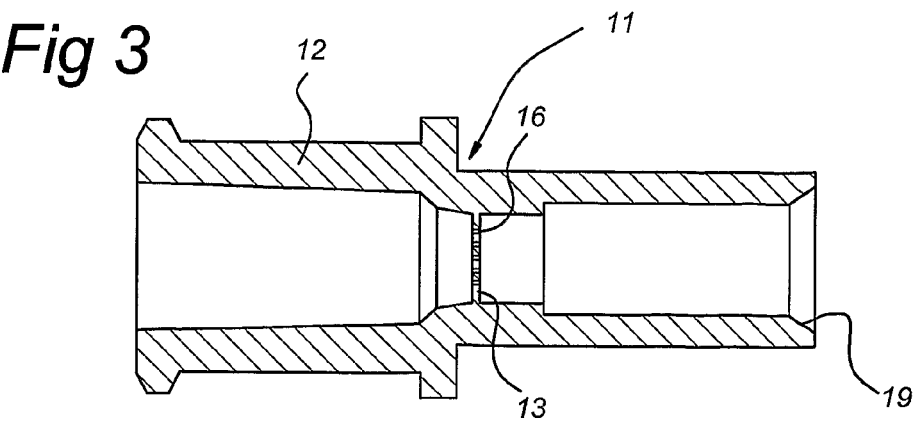
FIG. 3 shows, in cross-section, a second embodiment of the restriction according to the invention.

A further embodiment of the invention is shown in FIG. 3. The restriction is indicated by 11, whilst the conduit part thereof is indicated by 12. 13 is the baffle, whilst 16 are the openings made therein. With this arrangement the conduit part has been made as part of a coupling.

Figure 4:
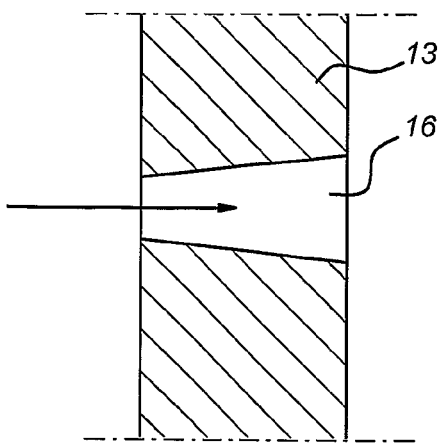
FIG. 4 shows a detail from FIG. 3.

Opening 16 is shown in detail in FIG. 4, from which it can be seen that this opening has been made conically divergent in the direction of flow. As a result clogging, for example by very small particles, such as bacteria, can be prevented.

Figure 5:
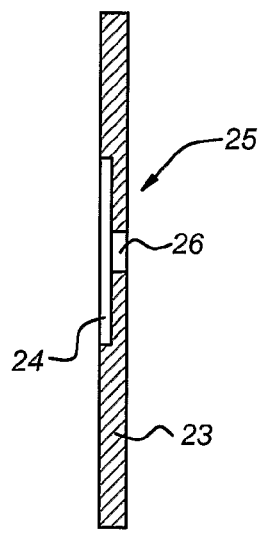
FIG. 5 shows a further variant of the restriction according to the invention.

A further variant of the restriction according to the invention is shown in FIG. 5. This variant is indicated in its entirety by 25 and consists of a preferably circular hole 26 made in baffle 23. There is an elongated slot 24 in front of the circular hole 26. As a result of the use of such a slot, opening 26 remains accessible to liquid if particles which under normal circumstances would block opening 26 reach the baffle 23. The transverse dimension (perpendicular to the drawing) of opening 26 can be larger than, the same as or smaller than the transverse dimension of the slot 24.

Figure 6:
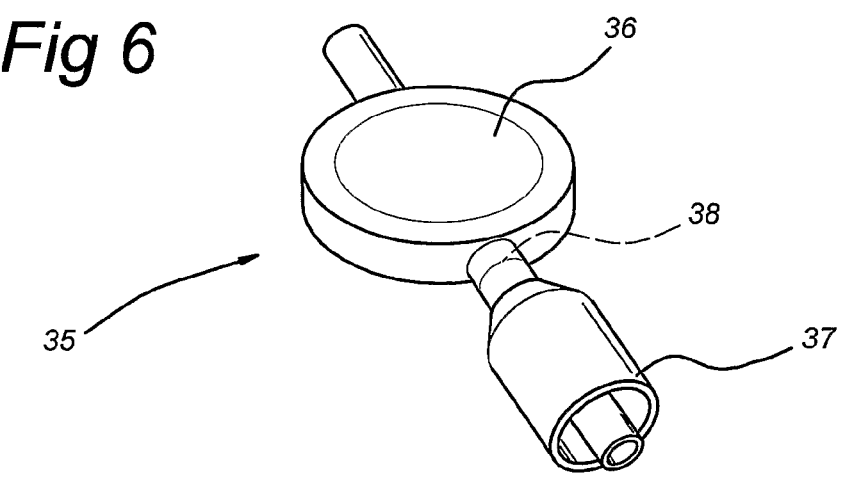
FIG. 6 shows another variant of the restriction according to the invention.

Another variant of the invention is shown in FIG. 6. This variant is indicated in its entirety by 35 and consists of a filter 36 and Luer fitting 37 connected after it and a construction according to the invention connected between the Luer fitting 37 and filter 36. This construction is indicated by 38 and made as described above. It can be seen from FIG. 6 that the restriction according to the invention can be integrated with many other components.

It has been found that by making a very large number of openings the blockage of one or more of the openings has hardly any effect. Furthermore, it has been found that highly predictable and reproducible flow properties can be achieved as a result of the very accurate production of the openings. This means that the present invention is suitable in particular for accurate metering. As indicated above, in this context consideration is given to medical application, such as when supplying fluids in the case of infusion and in the direct administration of, for example, analgesics. The present invention can also be used outside the medical field, for example when metering pesticides. Using the present invention it is possible accurately to control dosages of, for example, half a milliliter to one hundred milliliters water per hour.

Although the invention has been described above with reference to preferred embodiments, it will be understood that numerous modifications can be made thereto and many variants are possible. In particular, the conduit part can be modified in many ways so as to be part of a larger construction in which the baffle 3, 13, 23 has been integrated. These and further modifications are obvious to those skilled in the art after reading the above description and fall within the scope of the appended claims.

The invention claimed is:

1. A flow restriction device configured to be fitted in a fluid line, the restriction device comprising a conduit part provided with a baffle which includes an opening that links an upstream and downstream section of said line, wherein said opening in said baffle has a diameter dimension of between 1 µm and 50 µm, the thickness of said baffle being in the range of 0.05 mm and 0.5 mm, said conduit part and said baffle being produced from one piece of plastic materials, and the ratio of the thickness of said baffle to the diameter of said opening being greater than 10, such that liquid flow through said flow restriction is laminar.

2. Flow restriction according to claim 1, having at least two openings.

3. Flow restriction according to claim 1, wherein said opening has a diameter dimension of between 5 and 40 um.

4. Flow restriction according to claim 1, wherein said baffle has a thickness of between 0.1 and 0.3 mm.

5. Flow restriction according to claim 1, wherein there are at least ten openings.

6. Flow restriction according to claim 1, wherein said opening is conical, with the axis of the cone coincident with the axis of the opening, and said opening widens in the direction of flow of said fluid.

7. Flow restriction according to claim 1, comprising polycarbonate material.

8. Flow restriction according to claim 1, wherein said conduit part is designed to receive a further line.

9. Flow restriction according to claim 8, having a self-seeking edge.

10. Flow restriction according to claim 1, wherein said conduit part comprises a coupling piece.

11. Flow restriction according to claim 1, having identification means.

12. Flow restriction according to claim 1, wherein said baffle extends essentially perpendicularly to said conduit part.

13. Flow restriction according to claim 1, wherein said opening has a slot.

14. A metering device having a flow restriction for regulating fluid flow through a fluid line, the device comprising a conduit part provided with a baffle having an opening, which links an upstream and downstream section of said line, wherein said opening in said baffle has a diameter dimension of between 1 μm and 50 μm, the thickness of said baffle being in the range of 0.05 mm and 0.5 mm, said conduit part and said baffle being produced from one piece of plastic material, and wherein the ratio of the thickness of said baffle to the diameter of said opening is greater than 10, such that the fluid flow through said flow restriction is laminar.

15. Metering device according to claim 14, comprising a medical metering device.

* * * * *